United States Patent
Capon et al.

(10) Patent No.: US 8,721,726 B2
(45) Date of Patent: May 13, 2014

(54) GLENOID IMPLANT

(75) Inventors: Didier Capon, Sautron (FR); Martin Gonzalvez, Dijon (FR); Franck Handelberg, Beersel (BE); Albert Isidro, Badalona Barcelona (ES); Damien Laques, Pujols (FR); Hugues De La Selle, Chalon sur Saone (FR); François Vedel, Aix en Provence (FR); Christophe Alepee, Lyons (FR)

(73) Assignee: Aston Medical Developments Limited, London (GB)

( * ) Notice: Subject to any disclaimer, the term of this patent is extended or adjusted under 35 U.S.C. 154(b) by 0 days.

(21) Appl. No.: 13/142,747

(22) PCT Filed: Dec. 28, 2009

(86) PCT No.: PCT/FR2009/052711
§ 371 (c)(1),
(2), (4) Date: Dec. 9, 2011

(87) PCT Pub. No.: WO2010/076534
PCT Pub. Date: Jul. 8, 2010

(65) Prior Publication Data
US 2012/0089233 A1  Apr. 12, 2012

(30) Foreign Application Priority Data
Dec. 29, 2008 (FR) .................................... 08 59102

(51) Int. Cl.
A61F 2/40 (2006.01)
(52) U.S. Cl.
USPC ...................................................... 623/19.11

(58) Field of Classification Search
USPC .......... 623/19.13, 19.14, 22.31, 22.32, 22.11, 623/22.15, 19.11, 19.12
See application file for complete search history.

(56) References Cited

U.S. PATENT DOCUMENTS

| | | | | |
|---|---|---|---|---|
| 5,489,310 | A * | 2/1996 | Mikhail | 623/19.11 |
| 7,445,638 | B2 * | 11/2008 | Beguin et al. | 623/19.14 |
| 2005/0261775 | A1 * | 11/2005 | Baum et al. | 623/19.12 |
| 2007/0038302 | A1 | 2/2007 | Shultz et al. | |
| 2007/0173945 | A1 * | 7/2007 | Wiley et al. | 623/19.13 |
| 2007/0244564 | A1 * | 10/2007 | Ferrand et al. | 623/19.13 |
| 2007/0260321 | A1 | 11/2007 | Stchur | |
| 2008/0208348 | A1 * | 8/2008 | Fitz | 623/19.14 |

FOREIGN PATENT DOCUMENTS

| | | | |
|---|---|---|---|
| EP | 0 339 530 | A2 | 11/1989 |
| EP | 0 581 667 | A | 2/1994 |
| EP | 1 402 853 | A | 3/2004 |
| EP | 1402853 | A2 * | 3/2004 |
| FR | 2825263 | A1 * | 12/2002 |
| GB | 2297257 | A * | 7/1996 |
| WO | 2006/086606 | A | 8/2006 |

OTHER PUBLICATIONS

International Search Report for PCT/FR2009/052711 dated Jun. 2, 2010.

* cited by examiner

*Primary Examiner* — Bruce E Snow
(74) *Attorney, Agent, or Firm* — Heslin Rothenberg Farley & Mesiti P.C.

(57) ABSTRACT

A cup intended to interact with a prosthetic humeral head has a generally circular shape and positioning and anchoring devices for embedding the cup in an anatomical glenoid cavity in such a way that a load-bearing and sliding surface of the cup is integrated into the continuity of the anatomical cavity so as to be perfectly congruent with the humeral head.

8 Claims, 3 Drawing Sheets

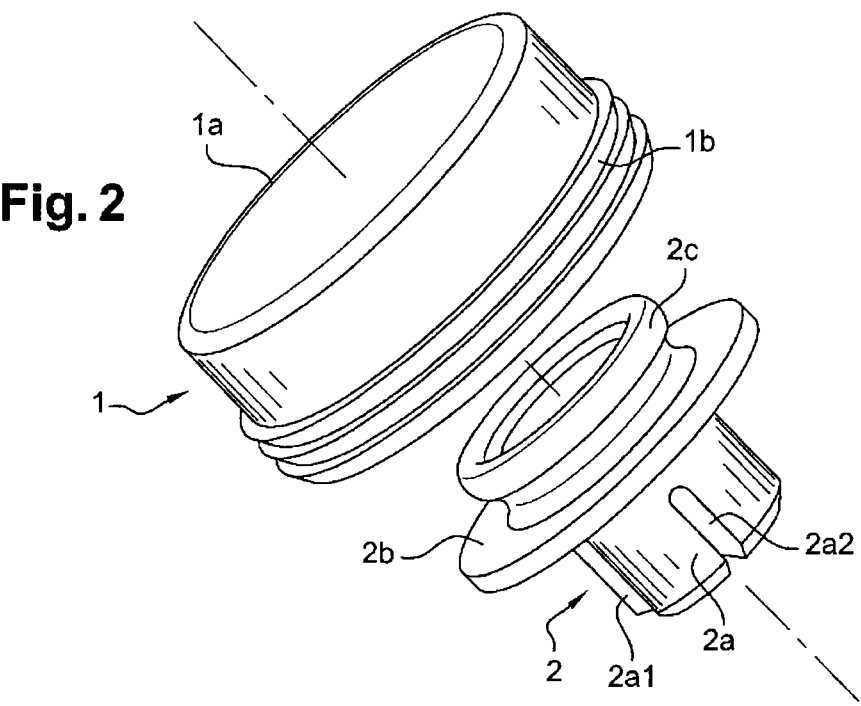
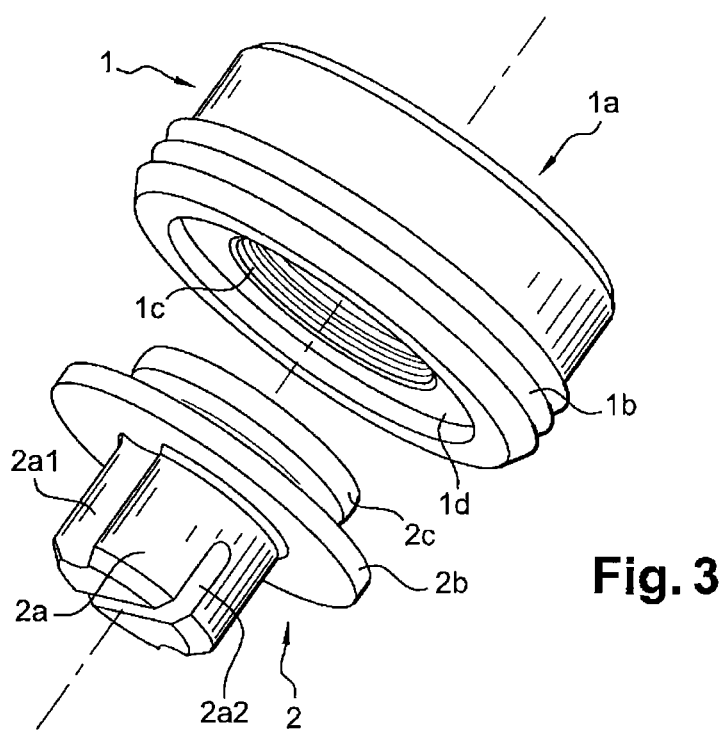

GLENOID IMPLANT

CROSS REFERENCE TO RELATED APPLICATIONS

This application is a national stage filing under section 371 of International Application No. PCT/FR2009/052711, filed on Dec. 28, 2009, and published in French on Jul. 8, 2010, as WO 2010/076534 and claims priority of French application No. 0859102 filed on Dec. 29, 2008, the entire disclosure of these applications being hereby incorporated herein by reference.

BACKGROUND ART

The invention comes within the technical field of orthopaedic implants.

More particularly, the invention concerns arthroplasty of the shoulder joint, particularly treatment of centred glenohumeral osteoarthritis.

In a way well known to those working in the field, the surgeon implants a glenoid prosthesis to compensate for the wear in an arthritic glenoid.

Essentially, this type of prosthesis generally consists of either a cemented polyethylene cup or a non-cemented tray to receive a polyethylene cup which will be in contact with a prosthetic humeral head, with which it will articulate.

It has been found that this type of prosthesis has disadvantages given that there is a tendency for the joint to be lateralised, which as a consequence modifies the centres of rotation of the shoulder leading to a breakout torque between the point at which the effort is applied by the head of the humerus and its fixation on the glenoid. A lever arm results composed of the thickness of the polyethylene cup which is in the order of 6 mm when it is cemented and 8 to 9 mm when the cup is combined, as indicated, with a tray. This lever arm forms a not insignificant breakout torque which can lead to premature loosening.

Recent biomechanical studies have demonstrated that the instantaneous centre of rotation is situated within an area of 5 to 8 mm diameter and does not follow translation consistent with rotation of the joint, as earlier publications would have it and has been generally accepted by surgeons.

Based on this observation, the problem that the invention proposes to solve is simply that of replacing the cartilage, without modifying the biomechanical architecture.

BRIEF SUMMARY OF INVENTION

To solve such a problem, a glenoid implant has been designed and developed consisting of a cup to interact with a prosthetic humeral head.

According to the invention, the cup is generally circular in shape and has appropriate positioning and fixation devices so that it can be embedded in the thickness of the anatomical glenoid cavity in such a way that the load-bearing and sliding surface of the said cup is integrated into the continuity of the said anatomical cavity so as to be perfectly congruent with the humeral head.

To resolve the problem of fixing the cup in the spongy bone of the glenoid, the cup has deformable stabilization lamellae extending from its periphery which interact with the spongy bone.

In an advantageous embodiment, the cup is attached to a tray, itself embedded, with a lug to anchor it in the cavity. The cup and tray are shaped in a complementary way to allow attachment. The cup has a recess which interacts with a flange on the tray.

Given the shear forces of the head of the humerus on the cup, the lug is provided with opposite anti-rotation notches and a transverse slot allowing it to be embedded in the spongy bone of the glenoid.

BRIEF DESCRIPTION OF THE DRAWING FIGURES

The invention is explained below in more detail with the aid of the attached diagrammatic figures in which:

FIGS. 2 and 3 are views in perspective before mounting the cup on the tray;

DETAILED DESCRIPTION

Figure 1:
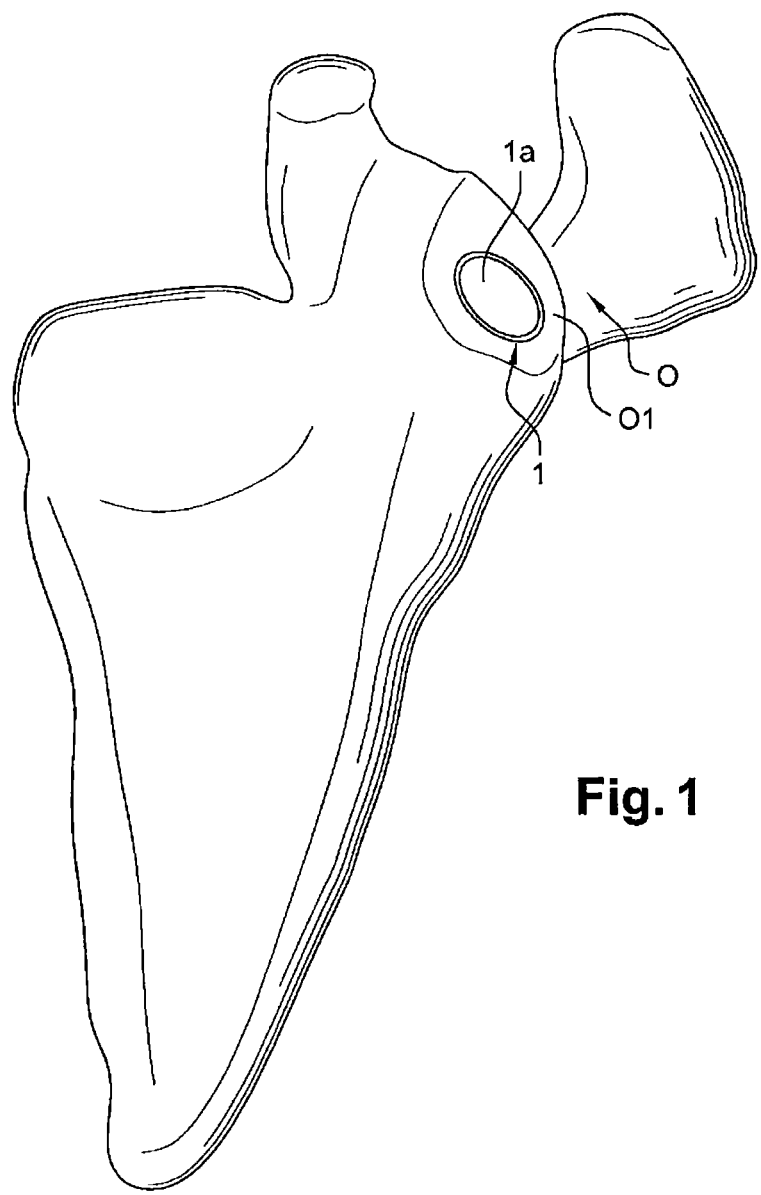
FIG. 1 is a diagrammatic view of a scapula in which the anatomical glenoid cavity is fitted with an implant according to the invention.
Figure 4:
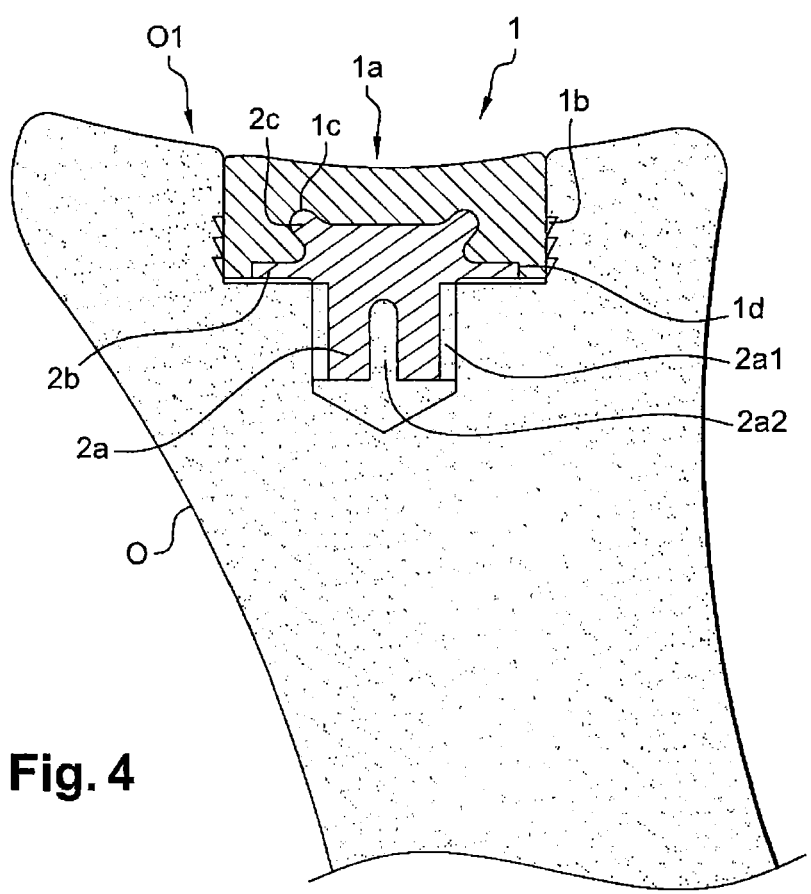
FIG. 4 is a sectional view showing the fixation of a glenoid implant according to the invention, in a site in the anatomical glenoid cavity.

The scapula, shown in FIG. 1 is labelled as (O), whereas the anatomical glenoid cavity which will receive the implant is labelled as (O1).

According to a basic characteristic of the invention, the glenoid implant is made to be embedded in the glenoid cavity, with the objective of simply replacing the cartilage, without modifying its biomechanical architecture.

The implant comprises a polyethylene cup (1) with a concave load-bearing and sliding surface (1a) for the articulation of the prosthetic humeral head (not shown).

According to the invention, the cup (1) has positioning and fixation devices, e.g., deformable stabilization lamellae (1b), complementary shapes (1c), and/or recess (1d) described below, for it to be embedded in a site of complementary shape made in the spongy bone of the glenoid cavity (O1). After fixation, the load-bearing and sliding surface (1a) of the cup (1), which is generally round in shape, is congruent with the anatomical cavity of the glenoid.

In other words, the cup (1) integrates into the continuity of the anatomical cavity.

As shown particularly in FIGS. 2 and 3, extending from its periphery, the cup has deformable stabilization lamellae (1b) interacting with the spongy bone. To advantage, the cup (1) is attached to a tray (2) which has an anchoring lug (2a) which fits into a hole made in the thickness of the glenoid cavity receiving the cup (1). The cup (1) and the tray (2) have complementary attachment shapes (1c) and (2c). For example, the tray (2) has a circular supporting flange (2b) produced coaxially with the lug (2a), which has projecting shapes (2c) on the outside which clip, under considerable force, into the complementary shapes (1c) of the cup (1).

It should be noted that the cup (1) has a recess (1d) into which the supporting flange (2b) of the tray (2) fits.

To create an anti-rotation effect under the shearing forces of the head of the humerus on the cup (1), the lug (2a) has notches (2a1) e.g. diametrically opposed to one another. It should be noted that the supporting surface of the flange (2b) of the tray (2) and the external surface of the lug (2a) can receive a bioconductive coating.

To advantage, the lug (2a) also has one or two transverse notches (2a2) allowing it to be embedded in the spongy bone of the glenoid, thus preventing rotation and increasing the surface of interaction with the glenoid.

The advantages are clear from the description. In particular it should be borne in mind and emphasized even that the resurfacing implant according to the characteristics of the invention simply replaces the cartilage, without modifying the biomechanical architecture, taking into account the fact that the centre of rotation is situated within an area of 5 to 8 mm in diameter.

The invention claimed is:

1. A resurfacing glenoid implant comprising a cup having a load bearing and sliding surface with a completely circular edge at one end intended to interact with a prosthetic humeral head, wherein the cup has a circular cylindrical periphery extending away from all of said completely circular edge of said load-bearing and sliding surface and positioning and fixation devices for embedding all of the cup in an anatomical glenoid cavity of a scapula in such a way that the load-bearing and sliding surface of the cup is integrated into and flush with a continuity of said anatomical glenoid cavity so as to be congruent with the prosthetic humeral head, the cup is attached to a tray having a lug for anchorage in the cavity, height of the cup and attached tray and lug is not greater than height of the anatomical glenoid cavity, and the cup has deformable stabilization lamellae extending laterally from the circular cylindrical periphery of the cup to interact with spongy bone of the anatomical glenoid cavity.

2. Implant according to claim 1, wherein the cup and the tray have complementary attachment shapes.

3. Implant according to claim 1, wherein the cup has a recess interacting with a circular flange on the tray.

4. Implant according to claim 1, wherein the lug has opposite anti-rotation notches.

5. Implant according to claim 1, wherein the lug has at least one transverse notch extending along and fully across a bottom surface of the lug.

6. Implant according to claim 1, wherein the cup has a circular cross-sectional shape.

7. Implant of claim 1, wherein the continuity of the anatomical glenoid cavity comprises an outer surface of the scapula adjoining the anatomical glenoid cavity.

8. Implant according to claim 1, wherein the cup is immovably attached to the tray.

* * * * *